United States Patent [19]

Yoshihara

[11] Patent Number: 4,752,888
[45] Date of Patent: Jun. 21, 1988

[54] METHOD OF DETERMINING MAJOR AND MINOR PEAKS IN A CHROMATOGRAM USING A DATA PROCESSOR

[75] Inventor: Touhachi Yoshihara, Katsuta, Japan

[73] Assignee: Hitachi, Ltd., Tokyo, Japan

[21] Appl. No.: 809,199

[22] Filed: Dec. 16, 1985

[30] Foreign Application Priority Data

Dec. 19, 1984 [JP] Japan .................. 59-267875

[51] Int. Cl.⁴ .................. G06G 7/00; G06F 15/31
[52] U.S. Cl. .................. 364/497; 364/565; 364/487
[58] Field of Search .............. 364/497, 498, 525, 565, 364/566, 715, 487

[56] References Cited

U.S. PATENT DOCUMENTS 4,183,087  1/1980  Huelsman ............... 364/487
4,580,227  4/1986  Lavergnat et al. ....... 364/487

Primary Examiner—Parshotam S. Lall
Assistant Examiner—Daniel W. Juffernbruch
Attorney, Agent, or Firm—Antonelli, Terry & Wands

[57] ABSTRACT

A data processor for chromatography operates to separately recognize the peaks of a composite peak of a chromatogram. At first, in order to separate the peaks, the maximum point of the peak of the chromatogram is determined, and extrapolation lines are drawn from said maximum point to the individual points of the chromatogram, and then the gradients of the lines changing from the minimum to the maximum are determined. By determining the changes of the gradients of the extrapolation lines and intersection points of the extrapolation lines and the chromatogram, the major and minor peak are separated so that the shoulder peak can be judged remarkably accurately.

6 Claims, 3 Drawing Sheets

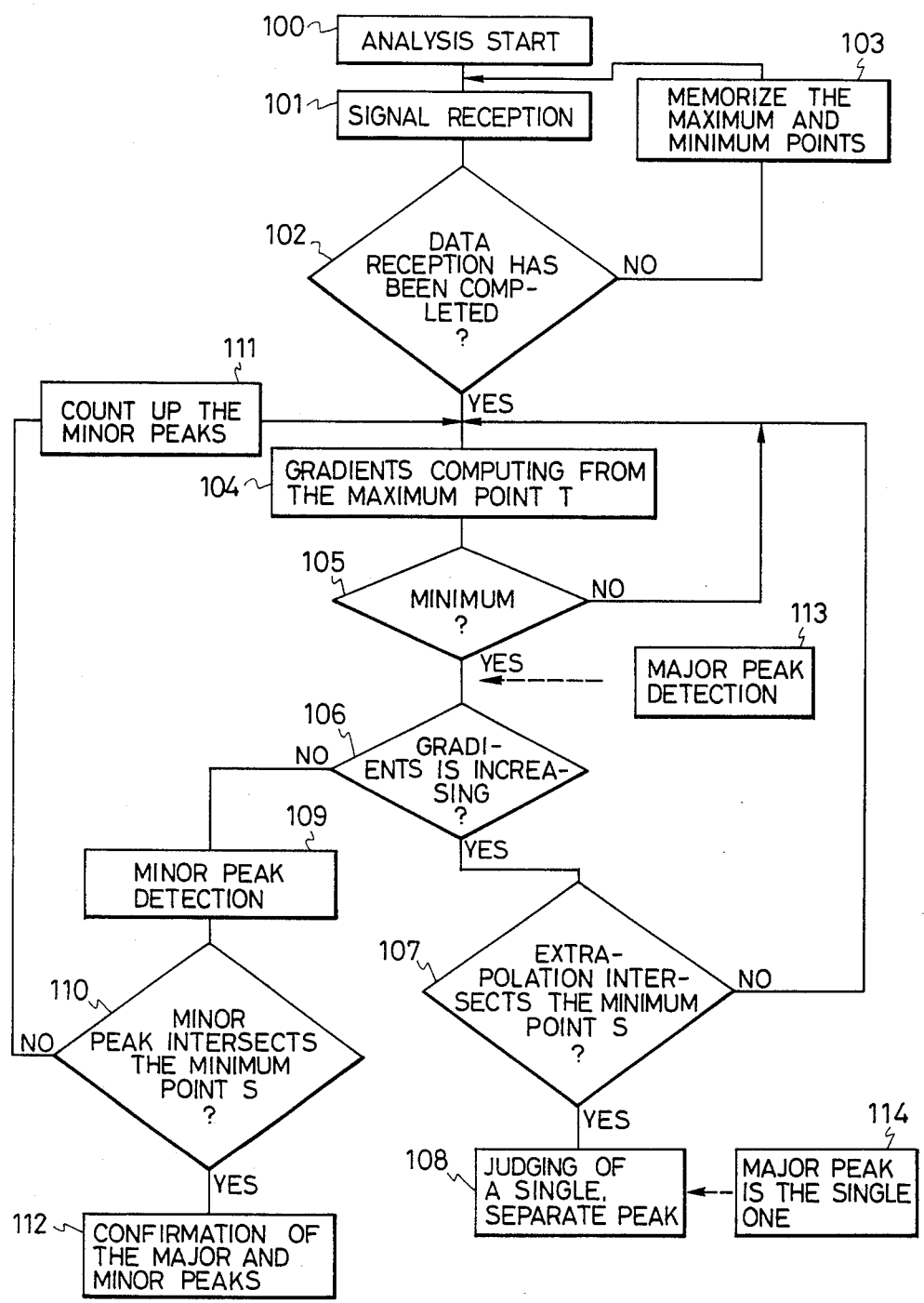

METHOD OF DETERMINING MAJOR AND MINOR PEAKS IN A CHROMATOGRAM USING A DATA PROCESSOR

BACKGROUND OF THE INVENTION

The present invention relates to a data processor for chromatography such as a gas or liquid chromatograph and, more particularly, to a data processor for chromatography, which can detect the shoulder peak of a chromatogram without fail.

The data processor for chromatography of the prior art has generally adopted the method of detecting a gradient of a peak in terms of the changing rate of a graph per unit time as the method of judging the starting point and ending point of the peak to judge the shape of the peak. One example of this prior art is disclosed in Japanese patent publication No. 53-40508. However, the peak judging method disclosed has failed to separate two peaks from a composite peak, in which the two peaks are so superposed that they cannot be sufficiently separated. This is because the judgement of the rise of the peak is conducted by detecting the gradient so that errors are caused in the judgement depending upon the noise level of the signals. It is difficult to separate and judge a front shoulder peak (as indicated at point a in FIG. 5(A)) and a rear shoulder peak (as indicated at point b in FIG. 5(B)), for example.

SUMMARY OF THE INVENTION

An object of the present invention is to provide a data processor for chromatography, which is able to separately detect a shoulder peak without fail.

According to the present invention, all the chromatogram signals of a chromatograph are stored, and the gradients of extrapolations joining the maximum point of the individual peaks and the individual sampling points are determined. Then, the sampling point at which the extrapolation having the minimum gradient intersects is recognized as the point of inflection and accordingly as the starting point of a parent peak. It is also recognized that the point of inflection of the chromatogram is the shoulder peak being located, and this point is established when the extrapolation from the maximum point located as the sampling point descends from the former point of inflection, i.e., the starting point has its gradient changing again to decrease, and that the point of inflection, which is determined from the changes in the gradients of the extrapolations formed as the sampling point descends, is the starting point of the shoulder peak.

In these ways, in terms of the changes in the gradients made by the extrapolations extending from the maximum point of the chromatogram to the sampling points, the peaks are separately detected so that a highly accurate detection of the shoulder peak can be accomplished.

BRIEF DESCRIPTION OF THE DRAWINGS

FIG. 4 is a processing flow chart; and

DESCRIPTION OF THE PREFERRED EMBODIMENT

Figure 1:
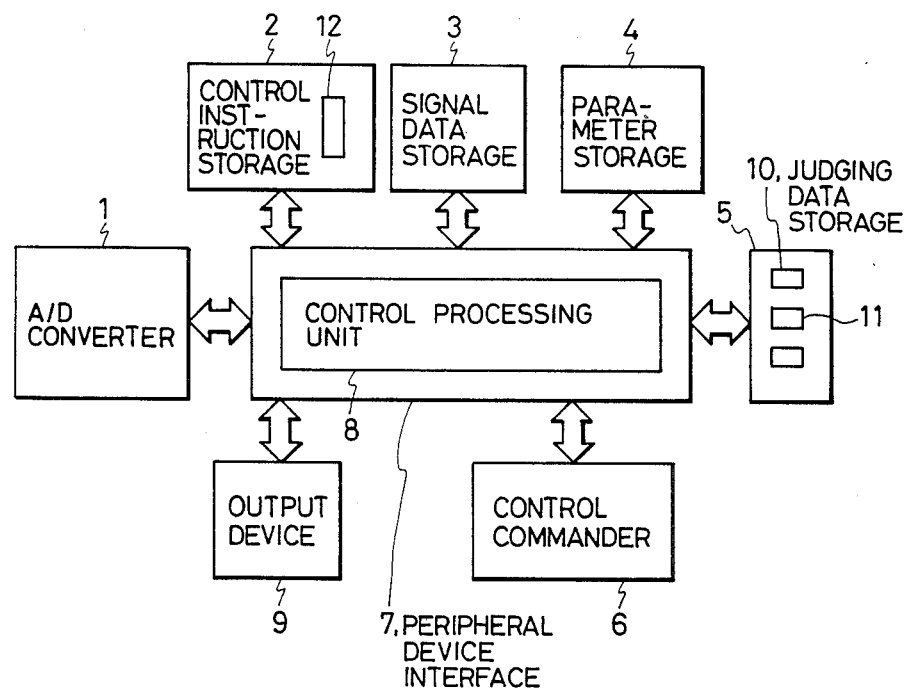
FIG. 1 is a block diagram showing the arrangement of one embodiment of the present invention.
Figure 2:
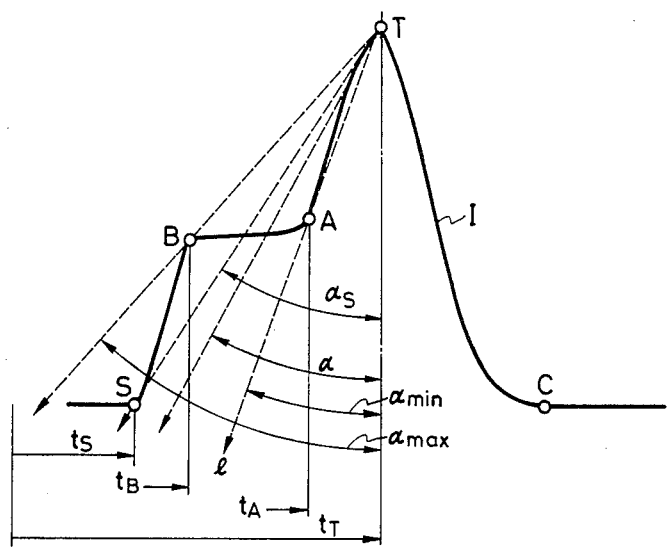
FIG. 2 is a diagram showing a chromatogram having the composite peak.

FIG. 1 shows the embodiment of the present invention. In FIG. 1: reference numeral 1 indicates an A/D converter for signals; numeral 2 a control instruction storage; numeral 3 a signal data storage; numeral 4 a parameter storage; numeral 5 a judging data storage; numeral 6 a control commander; numeral 7 a peripheral device interface; numeral 8 a central processing unit; numeral 9 an output device; numeral 10 a major peak judging data storage; numeral 11 a minor peak judging data storage; and numeral 12 a logic storage of the present invention. The analog signals concerning the chromatogram and coming from a chromatogram are converted through the A/D converter 1 to digital signals, which are fed through the peripheral device interface 7 to the central processing unit 8. In accordance with a program command in the control instruction storage, the digital signals are transformed into data of a predetermined type set by the control commander 6 stored with the processing conditions as can be computed, until the data transformed is stored in the signal data storage 3. At this time, moreover, the data is printed by the output device 9 when it reaches a predetermined quantity, i.e., the storage limit of the memory. And, these operations are repeated to form a chromatogram such as shown in FIG. 2. When one cycle of the storage of the chromatogram signals is thus ended, the peak judgement is then conducted.

This peak judgement according to the present invention will be described with reference to a graph I shown in FIG. 2. The peak to be described is a composite peak having a shoulder peak at its front, as shown.

1. Peak Information

The maximum point of the composite peak, at which the changing rate of the gradient of the graph per unit time turns to take a negative value, is designated at T, and the minimum point of the composite peak is designated at S. For the peak judgement, those two pieces of information are detected and stored in the judging data storage 5 of FIG. 1.

2. Peak Judgement

At a first step, a perpendicular is drawn joining the maximum point T and the time $t_T$ lying on the time axis.

At a second step, the stored sampling data of the chromatogram are sequentially read out backward from the maximum point time $t_T$ to the measurement starting time $t_s$, and the gradients $\alpha$ of the extrapolations l joining the maximum point T and the individual sampling points are measured with respect to the perpendicular of the point T.

At a third step, the minimum angle $\alpha_{min}$ of the gradients of the extrapolations l extending from the point T to the individual sampling points is detected, and the contact point A of the extrapolation l at the minimum angle $\alpha_{min}$ is located. The data $\alpha_{min}$ and the coordinates of the point A are stored in the major peak judging data storage 10 of FIG. 1. That point A provides the starting point of the major peak.

Figure 3:
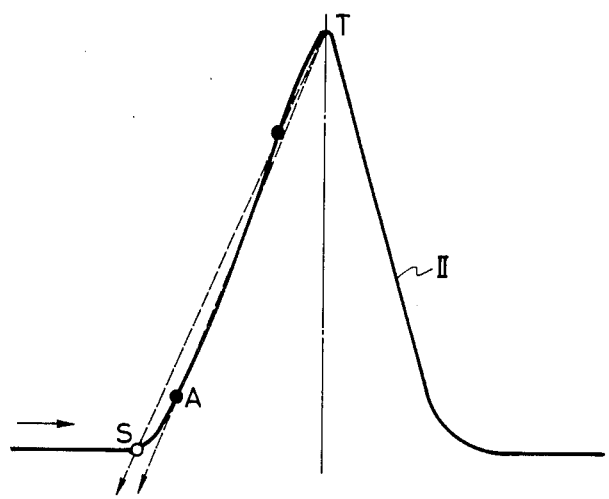
FIG. 3 is a graph showing a chromatogram having one peak.
Figure 5A:
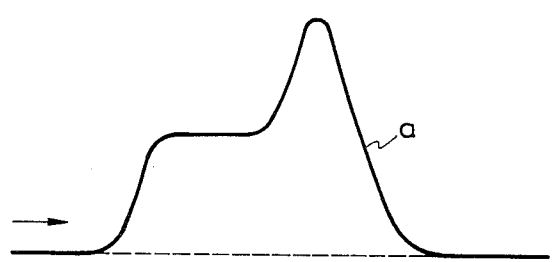
FIGS. 5(A) and 5(B) are graphs showing the chromatograms having the individual shoulder peaks.
Figure 5B:
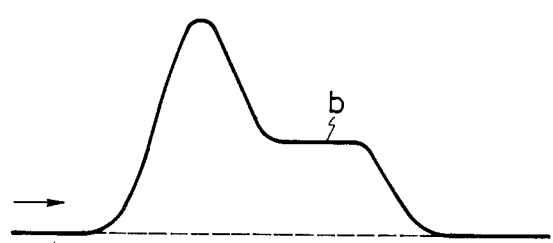

At a fourth step, after point A has been determined, the gradients $\alpha$ of the extrapolations to the sampling data are likewise checked to the minimum point S. If, at this time, the gradients $\alpha$ are gradually increased up to the minimum point S such that they arrive at the minimum point S, it can be judged that the peak is the single one shown in FIG. 3.

At a fifth step, if, after the minimum angle $\alpha_{min}$ has been determined in the course of the repetitions of the judgement of the foregoing fourth step, a gradient $\alpha_{max}$ (at a point B) is confirmed in the state where the extrapolations l between the point T and the sampling points have at least two or more points of intersection with the chromatography signal data sampled, and if the distance (or time period) from the point T has not reached the time $t_T$ yet, it is judged that there is another peak during that time period. And, the point B is stored as the maximum point of that peak in the minor peak judging data storage 11 of FIG. 1.

Next, the peak formations of the minor peak and the major peak are conducted in the following manner:

(1) Major Peak

Peak Starting Point: A;
Peak Top Point: T; and
Peak Ending Point: C.

(2) Minor Peak

Peak Starting Point: S;
Peak Top Point: B; and
Peak Ending Point: A.

Then, the peak shapes are judged by the method of the prior art. For another composite peak having a shoulder peak at its back, the shoulder peak can be accurately detected by a similar judgement.

FIG. 4 is a flow chart showing the processing steps described above. When the analysis is started at step 100, it is advanced in accordance with the program in the control command device 6 shown in FIG. 1. Next, at a step 101, the signal reception is conducted by the A/D converter 1 shown in FIG. 1, and it is judged at step 102 whether data reception has been completed. This completion of data reception is judged with reference to the data stored in the control instruction storage 2 and the parameter storage 4 both shown in FIG. 1. Moreover, the individual sampling data are judged till the end, and the minimum and maximum points are detected and stored in the judging data storage 5 shown in FIG. 1. When the data reception is completed, the gradients measured from the maximum point to the individual sampling values are computed.

Next, at a step 104, the gradients from the maximum point T are computed at logic storage 12 shown in FIG. 1. At a step 105, the minimum angle $\alpha_{min}$ f those computed gradients is determined through the extrapolations extending from the maximum point T to the individual sampling values. If that minimum angle $\alpha_{min}$ is determined, the major peak detection is marked at step 113. Next, at step 106, the magnitude of the gradients is checked. For an increasing gradient, it is judged at step 107 whether or not the extrapolation intersects the minimum point S. If it does, it is judged at step 108 that the major peak is a single, separate one. Then, the peak number one is counted at step 114.

If the minimum angle $\alpha_{min}$ is detected at step 105 and if it is judged at step 106 that the gradient is decreasing, the presence of the minor peak is marked at a step 109. Next, it is judged at step 110 whether or not the minor peak intersects the minimum point S. If it does not, the number of the minor peak is incremented at step 111, and the operation is returned to step 104. It is judged at step 110 that the minor peak has intersected the minimum point S, the number of the parent and minor peak is confirmed at a step 112.

These judgements are all executed by the actions of the logic storage 12 shown in FIG. 1.

As has been described hereinbefore, according to the present invention, the shoulder peak which has failed to be detected accurately in the prior art is detected by the absolutely novel method which resorts not to the detection of the slopes of the signals with respect to the time axis when the data is received but to the peak detection from the maximum point of the peak by restoring the peak at the end of the peak reception. As a result, there can be attained an effect that the shoulder peak can be accurately judged. Moreover, the single, separate peak can also be accurately judged as to its peak formation on the same principle.

What is claimed is:

1. A method of determining major and minor peaks in a chromatogram using a data processor having a storage device for storing data and processing unit responsive to stored programs for processing data stored in said storage device, comprising the steps of:

(a) storing in a time sequence data representing the successive points of a chromatogram of a sample in said storage device, said chromatogram having at least one peak;
   (b) detecting the maximum value of the data stored in said storage device and the location of the point having said maximum value in said time sequence by means of said processing unit so as to determine the location of said point of maximum value;
   (c) calculating the gradient of each of a plurality of lines which extend from said point of maximum value through respective points of said chromatogram located in said time sequence prior to said point of maximum value by using said processing unit; and
   (d) detecting whether both major and minor peaks occur in said chromatogram and determining the location of the minor peak by analyzing said detected gradients using said processing unit.

2. A method according to claim 1, wherein said determining of the location of a minor peak in said chromatogram is carried out by said processing unit by using the maximum and the minimum of said calculated gradients and the manner in which said gradients vary in said time sequence.

3. A method according to claim 2, wherein said determining of the location of a minor peak in said chromatogram is carried out by said processing unit by:

(d1) locating a minimum point on said chromatogram corresponding to the minimum value stored in said storage device occurring in said time sequence prior to said maximum value;
   (d2) locating a first intermediate point on said chromatogram through which a line having a gradient of minimum value passes;
   (d3) locating a second intermediate point on said chromatogram through which a line having a gradient of maximum value passes; and
   (d4) detecting that said second intermediate point is the apex of a minor peak by detecting when the gradients of lines passing through points on said chromatogram from said first intermediate point to said second intermediate point increase and the gradients of lines passing through points from said second intermediate point and minimum point decrease.

4. A method of determining major and minor peaks in a chromatogram using a data processor having a storage device for storing data and a processing unit responsive to stored programs for processing data stored in said storage device, comprising the steps of:
  (a) storing in a time sequence data representing the successive points of a chromatogram of a sample in said storage device, said chromatogram having at least one peak;
  (b) detecting the maximum value of the data stored in said storage device and the location of the point having said maximum value in said time sequence by means of said processing unit so as to determine the location of said point of maximum value;
  (c) calculating the gradient of each of a plurality of lines which extend from said point of maximum value through respective points of said chromatogram located in said time sequence subsequent to said point of maximum value by using said processing unit; and
  (d) detecting whether both major and minor peaks occur in said chromatogram and determining the location of the minor peak by analyzing said detected gradients using said processing unit.

5. A method according to claim 4, wherein said determining of the location of a minor peak in said chromatogram is carried out by said processing unit by using the maximum and the minimum of said calculated gradients and the manner in which said gradients vary in said time sequence.

6. A method according to claim 5, wherein said determining of the location of a minor peak in said chromatogram is carried out by said processing unit by:
  (d1) locating a minimum point on said chromatogram corresponding to the minimum value stored in said storage device occurring in said time sequence subsequent to said maximum value;
  (d2) locating a first intermediate point on said chromatogram through which a line having a gradient of minimum value passes;
  (d3) locating a second intermediate point on said chromatogram through which a line having a gradient of maximum value passes; and
  (d4) detecting that said second intermediate point is the apex of a minor peak by detecting when the gradients of lines passing through points on said chromatogram from said first intermediate point to said second intermediate point increase and the gradients of lines passing through points from said second intermediate point and minimum point decrease.

* * * * *